US012784901B2

(12) United States Patent
Masson et al.

(10) Patent No.: US 12,784,901 B2
(45) Date of Patent: Nov. 3, 2026

(54) SYSTEM AND METHOD FOR OPTIMIZING MEDICAL PROCEDURE USING INTERNET OF THINGS CAPABLE MEDICAL DEVICES

(71) Applicant: EXPANDED EXISTENCE, INC., Windermere, FL (US)

(72) Inventors: Robert L. Masson, Windermere, FL (US); Kyle A. Masson, Windermere, FL (US); Brett Luc Masson, Windermere, FL (US)

(73) Assignee: EXPANDED EXISTENCE, INC., Windermere, FL (US)

( * ) Notice: Subject to any disclaimer, the term of this patent is extended or adjusted under 35 U.S.C. 154(b) by 79 days.

(21) Appl. No.: 18/396,313

(22) Filed: Dec. 26, 2023

(65) Prior Publication Data

US 2025/0210184 A1 Jun. 26, 2025

(51) Int. Cl.

*G16H 40/20* (2018.01)
*G16H 40/63* (2018.01)
*G16Y 10/60* (2020.01)

(52) U.S. Cl.

CPC ............. *G16H 40/20* (2018.01); *G16H 40/63* (2018.01); *G16Y 10/60* (2020.01)

(58) Field of Classification Search

CPC ......... G16H 40/20; G16H 40/63; G16Y 10/60
See application file for complete search history.

(56) References Cited

U.S. PATENT DOCUMENTS

| | | | | |
|---|---|---|---|---|
| 11,471,227 | B1 * | 10/2022 | Roh | G16H 40/40 |
| 11,571,266 | B1 * | 2/2023 | Roh | A61B 90/98 |
| 2016/0120740 | A1 * | 5/2016 | Rawls-Meehan | A47C 31/008 601/49 |

(Continued)

FOREIGN PATENT DOCUMENTS

| | | |
|---|---|---|
| CN | 107910048 A | 4/2018 |
| CN | 110931114 A | 3/2020 |

(Continued)

OTHER PUBLICATIONS

PCT International Search Report dated Nov. 29, 2024 and the Written Opinion of the International Searching Authority issued in PCT/US2024/048675, filed Sep. 26, 2024.

*Primary Examiner* — Shahid Merchant
*Assistant Examiner* — David Choi
(74) *Attorney, Agent, or Firm* — Sagacity Legal PLLC

(57) ABSTRACT

A system for continuously optimizing a medical procedure includes a plurality of internet-of-things (IoT) capable medical devices and a server. Each IoT capable medical device is configured to provide medical output data associated with the medical procedure. The server is configured to receive the medical output data associated with the medical procedure and determine correlations between the medical output data of at least one IoT capable medical device and at least one another IoT capable medical device. The server is configured to obtain patient data and optimize the correlations to obtain optimized correlations based on the patient data. The server is configured to provide the optimized correlations to the at least one IoT capable medical device to optimize the medical procedure by adjusting medical input parameters associated with the at least one IoT capable medical device based on the optimized correlations.

16 Claims, 5 Drawing Sheets

(56) References Cited

U.S. PATENT DOCUMENTS

| | | | | |
|---|---|---|---|---|
| 2019/0125455 | A1* | 5/2019 | Shelton, IV | A61B 5/00 |
| 2019/0262084 | A1* | 8/2019 | Roh | A61B 34/20 |
| 2020/0275976 | A1* | 9/2020 | Mckinnon | G16H 20/40 |
| 2022/0181024 | A1 | 6/2022 | Palti et al. | |
| 2022/0223268 | A1 | 7/2022 | Masson et al. | |
| 2022/0233119 | A1* | 7/2022 | Shelton, IV | A61B 17/07207 |
| 2022/0377714 | A1 | 11/2022 | Liu et al. | |
| 2023/0078793 | A1 | 3/2023 | Mason | |
| 2023/0270562 | A1* | 8/2023 | Roh | G16H 30/40<br>606/1 |
| 2024/0215800 | A1* | 7/2024 | Shelton, IV | G06K 19/07749 |
| 2025/0222218 | A1* | 7/2025 | Dong | A61M 16/01 |

FOREIGN PATENT DOCUMENTS

| | | | |
|---|---|---|---|
| CN | 112102907 | A | 12/2020 |
| CN | 113380358 | | 9/2021 |
| CN | 113628737 | A | 11/2021 |
| CN | 115361424 | A | 2/2023 |
| CN | 113472845 | A | 5/2023 |
| IN | 202341026645 | | 5/2020 |
| WO | 2016006724 | A1 | 1/2016 |
| WO | 2022130006 | A1 | 6/2022 |

* cited by examiner

SYSTEM AND METHOD FOR OPTIMIZING MEDICAL PROCEDURE USING INTERNET OF THINGS CAPABLE MEDICAL DEVICES

BACKGROUND OF THE INVENTION

According to data from the National Center for Health Statistics, nearly fifty (50) million surgical inpatient procedures were performed in 2009 in the United States alone, and that number continues to grow. Optimization of those procedures is crucial for medical practitioner efficiency, patient safety, and team workflow. Regardless of how well trained the medical practitioner is, human error can occur, especially when performing procedures on different patients with different medical histories and different medical conditions.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention and explain various principles and advantages of those embodiments.

Figure 1:
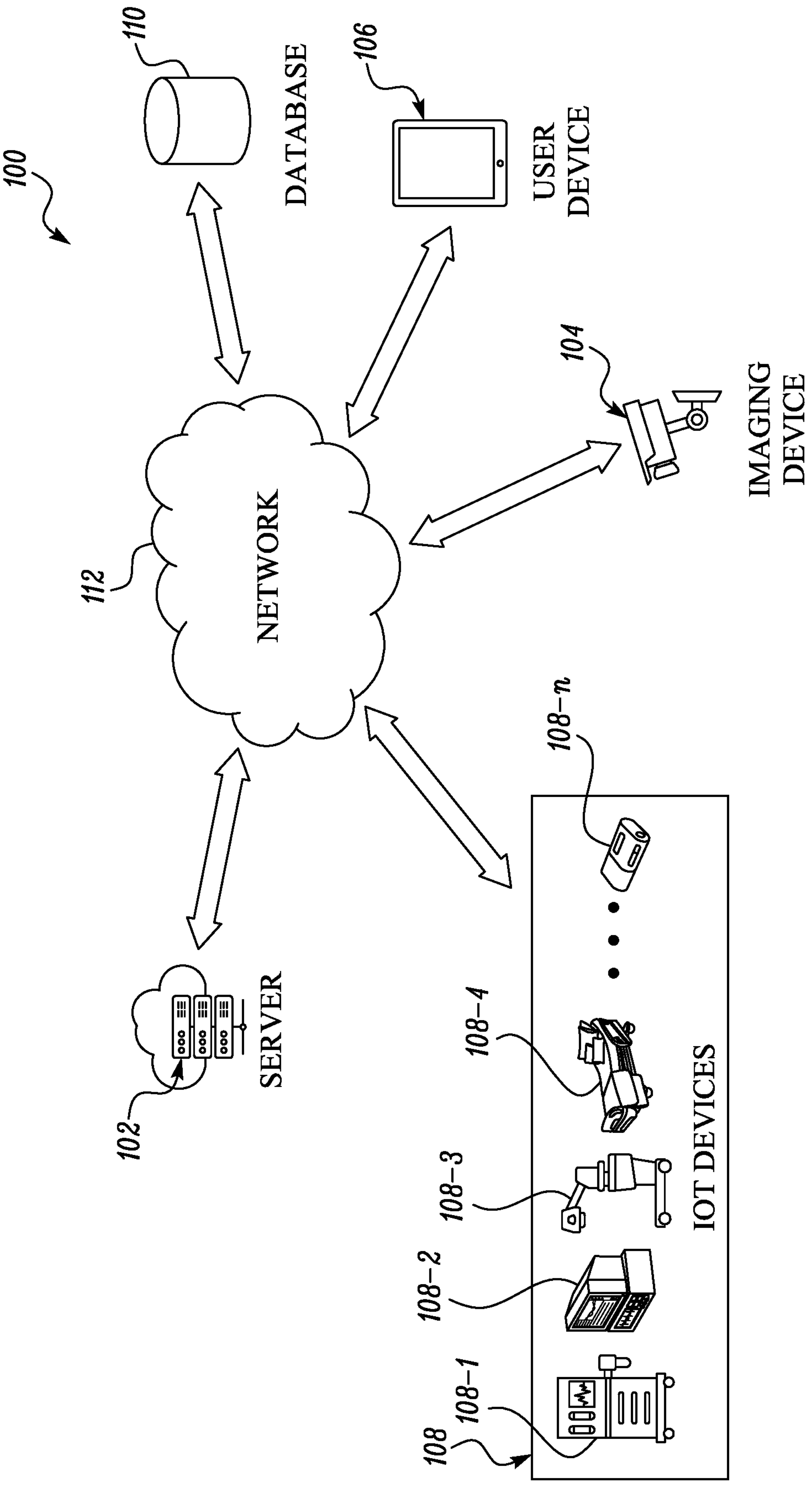
FIG. 1 is a block diagram of a system for optimizing medical procedure using internet-of-things (IoT) capable medical devices, in accordance with some embodiments.

Skilled artisans will appreciate that the elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

In one aspect, a system for continuously optimizing a medical procedure is described. The system includes a plurality of internet-of-things (IoT) capable medical devices and a server communicatively coupled to the plurality of IoT capable medical devices. Each IoT capable medical device of the plurality of IoT capable medical devices is configured to provide medical output data associated with the medical procedure. The server is configured to receive, by a server transceiver, the medical output data associated with the medical procedure from the plurality of IoT capable medical devices and determine, by a server processor, one or more correlations between the medical output data of at least one IoT capable medical device of the plurality of IoT capable medical devices and at least one another IoT capable medical device of the plurality of IoT capable medical devices using one or more machine learning models. The server is further configured to obtain, by the server processor, patient data associated with a patient undergoing the medical procedure and optimize, by the server processor, the one or more correlations between the medical output data of the at least one IoT capable medical device and the at least one another IoT capable medical device to obtain one or more optimized correlations based on the patient data using the one or more machine learning models. The server is further configured to provide, by the server transceiver, the one or more optimized correlations to the at least one IoT capable medical device to optimize the medical procedure by adjusting medical input parameters associated with the at least one IoT capable medical device based on the one or more optimized correlations with the at least one another IoT capable medical device.

In another aspect, a method for continuously optimizing a medical procedure is described. The method includes receiving, by a server, medical output data associated with the medical procedure from a plurality of internet-of-things (IoT) capable medical devices and determining, by the server, one or more correlations between the medical output data of at least one IoT capable medical device of the plurality of IoT capable medical devices and at least one another IoT capable medical device of the plurality of IoT capable medical devices using one or more machine learning models. The method further includes obtaining, by the server, patient data associated with a patient undergoing the medical procedure and optimizing, by the server, the one or more correlations between the medical output data of the at least one IoT capable medical device and the at least one another IoT capable medical device to obtain one or more optimized correlations based on the patient data using the one or more machine learning models. Further, the method includes providing, by the server, the one or more optimized correlations to the at least one IoT capable medical device to optimize the medical procedure by adjusting medical input parameters associated with the at least one IoT capable medical device based on the one or more optimized correlations with the at least one another IoT capable medical device.

FIG. 1 is a block diagram of a system 100 for continuously optimizing a medical procedure in accordance with various embodiments. The medical procedure corresponds to a plurality of steps that are to be carried out on a patient to improve health, treat a disease or injury or medical conditions, or make a diagnosis. For example, the medical procedure includes, but is not limited to, spinal surgery, scoliosis reduction, heart surgery, orthopedics, biopsy, or any type of procedure to diagnose, treat, or manage a medical condition, now known or in the future developed.

Referring to FIG. 1, the system 100 includes a server 102, an imaging device 104, a user device 106, a plurality of internet-of-things (IoT) capable medical devices 108 (for example, but not limited to, IoT capable medical devices 108-1, 108-2, 108-3, 108-4, . . . **108-*n*), and a database 110. In some embodiments, communication between the server 102, the imaging device 104, the user device 106, the IoT capable medical devices 108 (interchangeably referred to as IoT devices 108), and the database 110 occurs through a network 112. In some embodiments, the network 112** includes one or more networks 112, including one or more of a wide area network (WAN) (for example, a transport control protocol/internet protocol (TCP/IP) based network), a cellular network, and a local area network (LAN) employing any of a variety of communications protocols as is well known in the art or developed in the future.

In accordance with various embodiments, the medical procedure is performed by medical practitioner(s) and/or robotic system(s) using the IoT capable medical devices 108. The IoT capable medical devices 108 correspond to medical devices capable of collecting, providing, and/or adjusting data associated with one or more medical procedures. For example, each IoT capable medical device 108 is configured to collect medical output data associated with the medical procedure, provide the medical output data to one or more of the server 102, the database 110, and other IoT capable medical devices 108 via the network 112, and adjust its medical input parameters associated with the medical procedure. In accordance with various embodiments, the medical output data corresponds to an output (such as, but not limited to, an output value, an output waveform, an output state, an output image, an alert, and the like) of the IoT capable medical device 108 and the medical input parameter corresponds to one or more parameters (such as, but not limited to, a dosage, a duration, a set-up, and the like) provided as an input to the IoT capable medical device 108 for controlling operation of the IoT capable medical device 108. The IoT capable medical devices 108 include, but are not limited to, an anesthesia machine 108-1, an electrophysiological monitoring device 108-2, an X-ray machine 108-3, a smart bed 108-4, a drug delivery device **108-*n*, and various other IoT capable medical devices 108 now known or in the future developed. In accordance with various embodiments, optimizing the medical procedure includes adjusting medical input parameters associated with at least one IoT capable medical device 108 of the plurality of IoT capable medical devices 108 for improving the accuracy and efficiency of the medical procedure. In some embodiments, the medical output data includes medical output data associated with one or more medical procedures (similar to the medical procedure) performed prior to the medical procedure and provided by the IoT capable medical devices 108**.

The components and the functionality of the imaging device 104 are now described in detail. For ease of reference, only one imaging device 104 is described as a part of the system 100 shown in FIG. 1, however, it would be appreciated that the system 100 may include more than one imaging devices 104. In accordance with various embodiments, the imaging device 104 is configured to capture a plurality of video/image frames associated with execution of the medical procedures in a medical procedure room. Each video/image frame captures one or more parameters associated with one or more of medical item(s), the medical practitioner(s), and the robotic system(s) during the medical procedure. The parameters include a movement of the medical item(s), a positioning of the medical item(s), a movement of the medical practitioner(s) or the robotic system(s), and a positioning of the medical practitioner(s) or the robotic system(s). The imaging device 104 is any device capable of capturing video/image frames including continuous images or sequential still images of the one or more of the medical item(s), the medical practitioner(s), the robotic system(s), and the medical procedure room. For example, the imaging device 104 includes one or more of a low-angle camera, a wall-mounted camera, an augmented reality device, or any device, now known or in the future developed, which can capture video/image frames and/or record or generate videos/images of the one or more of the medical item(s), the medical practitioner(s), the robotic system(s), and the medical procedure room. The imaging device 104 transmits the video/image frames to the server 102 and/or the database 110.

In accordance with various embodiments, the imaging device 104 is installed in the medical procedure room for capturing the video/image frames associated with the execution of the medical procedure. The medical procedure room is any room that is used by the medical practitioner(s) and/or the robotic system(s) for performing the medical procedure and includes the medical item(s) along with the IoT capable medical devices 108 for use during the medical procedure. For example, the medical items include, but are not limited to, one or more auxiliary tables or stands (such as a Mayo stand), a surgical scissor, a surgical needle, a forceps, a surgical tweezer, and various other medical items, now known or in the future developed, for use by the medical practitioner(s) and/or the robotic system(s) during the medical procedure.

Referring back to FIG. 1, the database 110 stores the plurality of video/image frames associated with the medical procedure. For ease of reference, only one database 110 is described as a part of the system 100 shown in FIG. 1, however, it would be appreciated that the system 100 may include more than one databases 110. In some embodiments, the database 110 also stores the medical output data provided by the IoT capable medical devices 108 during the medical procedure and the one or more medical procedures performed prior to the medical procedure. In some embodiments, the database 110 also stores patient data associated with the patient undergoing the medical procedure. The patient data includes one or more of current health parameters and previous health parameters of the patient. For example, the current health parameters include, but are not limited to, temperature, blood pressure, heart rate, blood loss, respiratory rate, weight, and the like, of the patient. The previous health parameters include medical history such as, but not limited to, previous surgeries, illnesses, allergies, metabolism rate, medications, genetic conditions, and the like of the patient. In an embodiment, the patient data is manually stored by the user in the database 110, via the server 102 or the user device 106. In some embodiments, the patient data is obtained during the medical procedure from the IoT capable medical devices 108.

Figure 2:
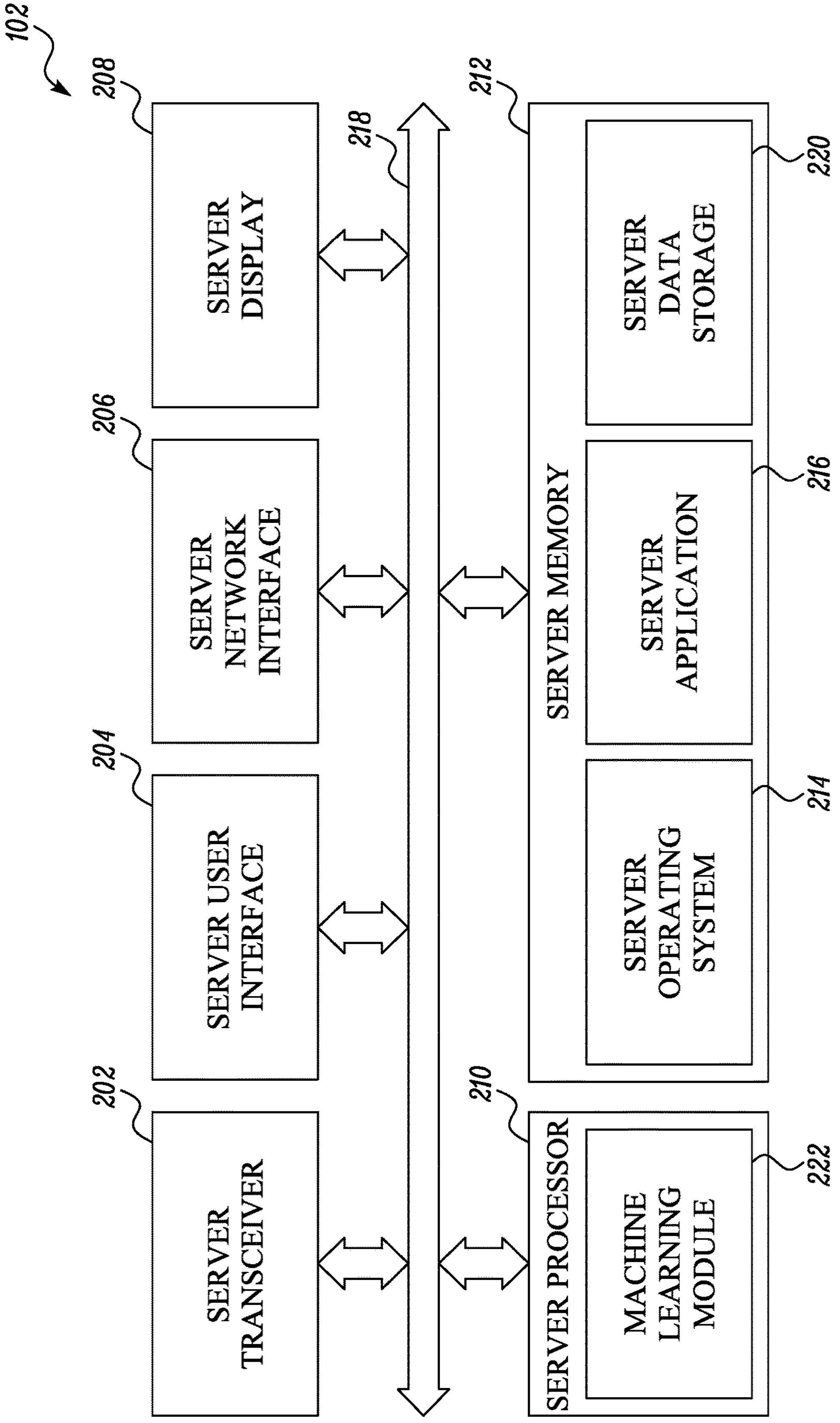
FIG. 2 is a block diagram of a server for use within the system of FIG. 1, in accordance with some embodiments.

The server 102 is configured to continuously optimize the medical procedure based on the medical output data provided by the IoT capable medical devices 108 and the patient data. For ease of reference, the components and the functionality of the server 102 are described in detail hereinafter with reference to FIG. 2. FIG. 2 is a block diagram of one exemplary embodiment of the server 102 for use within the system 100 of FIG. 1 in accordance with some embodiments. The server 102 is electrically and/or communicatively coupled to the imaging device 104, the user device 106, the IoT capable medical devices 108, and the database 110. In some embodiments, the server 102 includes a plurality of electrical and electronic components, for example, for providing power, operational control, and communication within the server 102. For example, in one embodiment, the server 102 includes, among other things, a server transceiver 202, a server user interface 204, a server network interface 206, a server display 208, a server processor 210, and a server memory 212.

It should be appreciated by those of ordinary skill in the art that FIG. 2 depicts the server 102 in a simplified manner and a practical embodiment includes additional components and suitably configured logic to support known or conventional operating features that are not described in detail herein. It will further be appreciated by those of ordinary skill in the art that the server 102 is a personal computer, a desktop computer, a tablet, an augmented reality device, a smartphone, a wearable device (wrist worn, eye worn), or any other server now known or in the future developed. It will further be appreciated by those of ordinary skill in the art that the server 102 alternatively functions within a remote server, a cloud server, or any other remote computing mechanism now known or in the future developed. Although the description below discusses the functions and operations performed by the server 102, a person skilled in the art would appreciate that, in some embodiments, the functions and operations of the server 102 can be performed in a single device or in a distributed manner by two or more devices without limiting the scope of the claimed subject matter.

The components of the server 102 (for example 202, 204, 206, 208, 210, and 212) are communicatively coupled via a server local interface 218. The server local interface 218 includes, for example, but not limited to, one or more buses or other wired or wireless connections, as is now known in the art or in the future developed. In an embodiment, the server local interface 218 has additional elements, which are omitted for simplicity, such as controllers, buffers (caches), drivers, repeaters, and receivers, among many others, to enable communications. Further, in some embodiments, the server local interface 218 includes address, control, and/or data connections to enable appropriate communications among the aforementioned components.

The server 102 in the illustrated example includes the server transceiver 202. The server transceiver 202, incorporating a server transceiver antenna (not shown), enables wireless communication between the server 102 and other devices, (for example, the imaging device 104, the user device 106, the IoT capable medical devices 108, and the database 110). It will be appreciated by those of ordinary skill in the art that the server 102 includes a single server transceiver 202 as shown, or alternatively separate transmitting and receiving components, for example, but not limited to, a transmitter, a transmitting antenna, a receiver, and a receiving antenna and/or any combination thereof.

The server user interface 204 is used to receive one or more user inputs from and/or for providing one or more system outputs from/to the user (for example, a medical practitioner) or from/to the user device 106. User input is provided via, for example, a keyboard, a touchpad, a mouse, a microphone, an augmented reality device, a camera, a headset, a Light Detection and Ranging (LiDAR) system, and/or any other user input now known or in the future developed, or any combination thereof. System output is provided via a server display 208, a server speaker (not shown), a printer (not shown) and/or any other system output now known or in the future developed, or any combination thereof. The server user interface 204 further includes, for example, a serial port, a parallel port, an infrared (IR) interface, a universal serial bus (USB) interface, a Bluetooth® interface, a wireless Fidelity (Wi-Fi) interface, a Near-field communication (NFC) interface, and/or any other interface for wired or wireless communication, now known or in the future developed.

The server network interface 206 is used to enable the server 102 to communicate on a network, such as, the network 112 of FIG. 1, a wireless access network (WAN), and a radio frequency (RF) network. The server network interface 206 includes, for example, an Ethernet card or adapter or a wireless local area network (WLAN) card or adapter. Additionally, or alternatively, the server network interface 206 includes a radio frequency interface for wide area communications, such as Long-Term Evolution (LTE) networks, or any other network now known or in the future developed. In an embodiment, the server network interface 206 includes address, control, and/or data connections to enable appropriate communications on the network. The server display 208 includes a display screen, a projector, a monitor or any other visual output device now known or in the future developed. In accordance with some embodiments, the server display 208 is configured to display any data, images, or information to the user.

The server memory 212 includes any non-transitory memory elements comprising one or more of volatile memory elements (for example, a random access memory (RAM), nonvolatile memory elements (for example, read-only memory "ROM"), and combinations thereof). Moreover, the server memory 212 incorporates electronic, magnetic, optical, and/or other types of storage media now known or in the future developed. Note that, in some embodiments, the server memory 212 has a distributed architecture, where various components are situated remotely from one another, but are accessed by the server processor 210. The software in the server memory 212 includes one or more software programs, each of which includes an ordered listing of executable instructions for implementing logical functions. The software in the server memory 212 includes a server operating system 214 and one or more server applications 216. The server operating system 214 controls the execution of other computer programs, such as, the one or more server applications 216, and provides scheduling, input-output control, file and data management, memory management, and communication control and related services. The one or more server applications 216 are configured to implement the various processes, algorithms, methods, techniques described herein.

In accordance with various embodiments, the one or more server applications 216 includes an image processing software to process and analyze the plurality of video/image frames obtained from the imaging device 104 to identify the medical item(s), the medical practitioner(s), the robotic system(s), and the medical procedure room in the plurality of video/image frames and determine the parameters. A person skilled in the art would appreciate that the image processing software can include a software that is capable of processing the plurality of video/image frames to identify the medical item(s), the medical practitioner(s), the robotic system(s), and the medical procedure room in the plurality of video/image frames and further determine the parameters associated with the medical item(s), the medical practitioner (s), and the robotic system(s).

In accordance with various embodiments, the one or more server applications 216 includes a speech recognition software to process and analyze the user input, such as, voice commands, provided by the user via the microphone. A person skilled in the art would appreciate that the speech recognition software can include a software that is capable of recognizing and processing the voice commands provided by the medical practitioner(s) via the microphone during the medical procedure.

The server memory 212 further includes a server data storage 220 used to store data. In the exemplary embodiment of FIG. 2, the server data storage 220 is located internal to the server memory 212 of the server 102. Additionally, or alternatively (not shown), the server data storage 220 is located external to the server 102 such as, for example, an external hard drive connected to the server user interface

204. In some embodiments (not shown), the server data storage 220 is located external and connected to the server 102 through a network and accessed via the server network interface 206. In some embodiments, the externally located server data storage 220 corresponds to the database 110 that stores one or more of the medical output data provided during the medical procedure and the one or more medical procedures performed prior to the medical procedure, the patient data, and the plurality of video/image frames. Alternatively, in other embodiments, the server data storage 220 and the database 110 are distinct independent storage units. In such cases, the medical output data, the patient data, and the plurality of video/image frames are stored either in the server data storage 220 or the database 110 or in a distributed manner in both the server data storage 220 and the database 110.

The server processor 210 is a hardware device for executing software instructions. In an embodiment, the server processor 210 is any custom made or commercially available processor, a central processing unit (CPU), an auxiliary processor among several processors associated with the server processor 210, a semiconductor-based microprocessor, or generally any device for executing software instructions now known or in the future developed. When the server 102 is in operation, the server processor 210 is configured to execute software stored within the server memory 212, to communicate data to and from the server memory 212, and to generally control operations of the server 102 pursuant to the software instructions.

The server processor 210 includes a machine learning module 222 having one or more machine learning models configured to determine one or more correlations between the medical output data of at least one IoT capable medical device of the plurality of IoT capable medical devices and at least one another IoT capable medical device of the plurality of IoT capable medical devices. The machine learning module 222 is further configured to optimize the one or more correlations based on the patient data associated with the patient undergoing the medical procedure. The machine learning module 222 is configured to learn and adapt itself to continuous improvement in changing environments. The machine learning module 222 employs any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. The machine learning module 222 implements an iterative learning process. The learning is based on a wide variety of learning rules or training algorithms now known or in the future developed. In an embodiment, the learning rules include, for example, one or more of back-propagation, pattern-by-pattern learning, supervised learning, and/or interpolation. The machine learning module 222 is configured to implement one or more machine learning algorithms to continuously optimize the medical procedure. In accordance with some embodiments of the invention, the machine learning algorithm utilizes any machine learning methodology, now known or in the future developed, for classification. For example, the machine learning methodology utilized includes one or a combination of: Linear Classifiers (Logistic Regression, Naive Bayes Classifier); Nearest Neighbor; Support Vector Machines; Decision Trees; Boosted Trees; Random Forest; and/or Neural Networks. The machine learning module 222 continually evolves specifics associated with steps included in the medical procedure in real time with new data inputs. The machine learning intent is to continually optimize the medical procedure.

In some embodiments, the user device 106 operates as a user interface for one or more users, such as, the medical practitioner(s), to provide user inputs and/or to approve adjustment of the medical input parameters of the IoT capable medical devices 108. For ease of reference, only one user device 106 is described as a part of the system 100 shown in FIG. 1, however, it would be appreciated that the system 100 may include more than one user devices 106.

Figure 3:
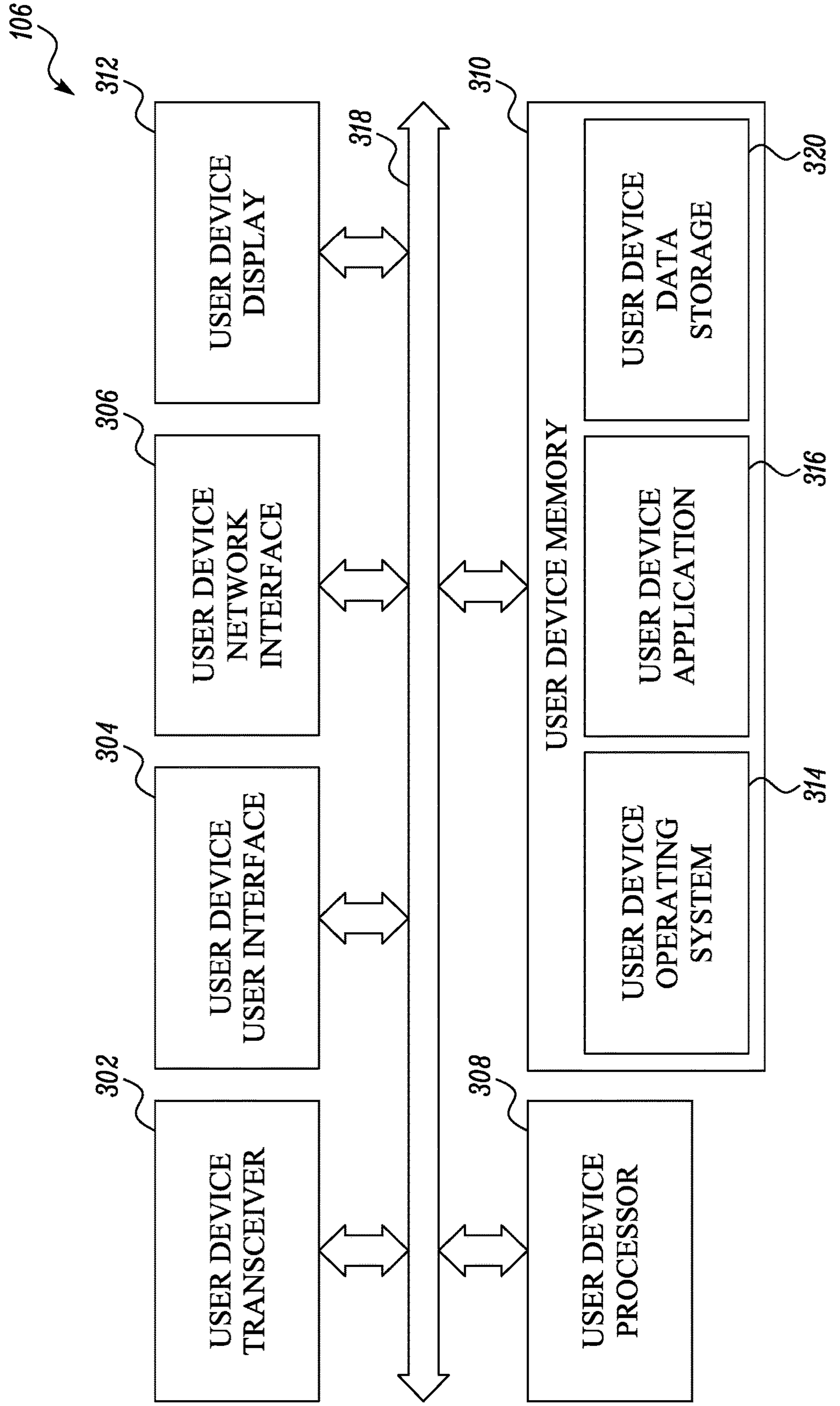
FIG. 3 is a block diagram of a user device for use within the system of FIG. 1, in accordance with some embodiments.

FIG. 3 is a block diagram of one exemplary embodiment of the user device 106 for use within the system 100 of FIG. 1. In accordance with some embodiments, the user device 106 is a tablet, a smartphone, an augmented reality or wearable device, or any other user device now known or in the future developed. In some embodiments, the user device 106 is electrically and/or communicatively coupled to a variety of other devices, for example, the server 102, the IoT capable medical devices 108, and the database 110. The user device 106 includes a number of electrical and electronic components, providing power, operational control, communication within the user device 106. For example, the user device 106 in one embodiment includes, among other elements, a user device transceiver 302, a user device user interface 304, a user device network interface 306, a user device processor 308, a user device memory 310, and a user device display 312. Although the description below discusses the functions and operations performed by the user device 106, a person skilled in the art would appreciate that, in some embodiments, the functions and operations of the user device 106 can be performed in a single device or in a distributed manner by two or more devices without limiting the scope of the claimed subject matter.

The components of the user device 106 (for example 302, 304, 306, 308, 310, 312) are communicatively coupled via a user device local interface 318. The user device local interface 318 includes, for example, but is not limited to, one or more buses or other wired or wireless connections, as is now known in the art or in the future developed. In an embodiment, the user device local interface 318 has additional elements, which are omitted for simplicity, such as controllers, buffers (caches), drivers, repeaters, and receivers, among many others, to enable communications. Further, in some embodiments, the user device local interface 318 includes address, control, and/or data connections to enable appropriate communications among the aforementioned components.

The user device 106 includes the user device transceiver 302. The user device transceiver 302 incorporating a user device transceiver antenna (not shown), enables wireless communication between the devices, for example, the server 102, the IoT capable medical devices 108, and the database 110 of FIG. 1. It will be appreciated by those of ordinary skill in the art that the user device 106 includes a single user device transceiver 302 as shown, or alternatively separate transmitting and receiving components, for example but not limited to, a transmitter, a transmitting antenna, a receiver, and a receiving antenna and/or any combination thereof.

The user device user interface 304 is used to receive input from the server 102, the IoT capable medical devices 108, and the database 110 and/or for providing system output from/to the user (for example, the medical practitioners) or from/to the one or more devices. The user device user interface 304 includes one or more input devices, including but not limited to a navigation key, a function key, a microphone, an augmented reality device, a camera, a headset, a Light Detection and Ranging (LiDAR) system, a voice recognition component, a joystick, or any other mechanism capable of receiving an input (hereinafter interchangeably referred to as the user input) from a user now known or in the future developed, or any combination thereof. Further, the user device user interface 304 includes one or more output devices, including but not limited to a speaker, headphones, a display, or any other mechanism capable of presenting an output to a user now known or in the future developed, or any combination thereof. In some embodiments, the user device user interface 304 includes a user interface mechanism, such as a touch interface or gesture detection mechanism that allows a user to interact with the displayed output. The user device display 312 is a separate user interface or combined within the user device user interface 304 for displaying information, such as, a notification for approving the adjustment of the medical input parameters of the IoT capable medical devices 108.

The user device network interface 306 is used to enable the user device 106 to communicate on a network, such as, the network 112 of FIG. 1, a wireless access network (WAN), and a radio frequency (RF) network. In an embodiment, the user device network interface 306 includes, for example, an Ethernet card or adapter or a wireless local area network (WLAN) card or adapter. Additionally, or alternatively, the user device network interface 306 includes a radio frequency interface for wide area communications such as Long-Term Evolution (LTE) networks, or any other network now known or in the future developed. In some embodiments, the user device network interface 306 includes address, control, and/or data connections to enable appropriate communications on the network 112.

The user device memory 310 includes any non-transitory memory elements comprising one or more of volatile memory elements (for example, a random access memory (RAM), nonvolatile memory elements (for example, read-only memory "ROM"), and combinations thereof). Moreover, in some embodiments, the user device memory 310 incorporates electronic, magnetic, optical, and/or other types of storage media now known or in the future developed. Note that, in an embodiment, the user device memory 310 has a distributed architecture, where various components are situated remotely from one another but are accessed by the user device processor 308. The software in the user device memory 310 includes one or more software programs, each of which includes an ordered listing of executable instructions for implementing logical functions. The software in the user device memory 310 includes a suitable user device operating system 314 and one or more user device applications 316. The user device operating system 314 controls the execution of other computer programs, such as, the one or more user device applications 316, and provides scheduling, input-output control, file and data management, memory management, and communication control and related services. The one or more user device applications 316 are configured to implement the various processes, algorithms, methods, and techniques described herein.

The user device memory 310 further includes a user device data storage 320 used to store data. In the exemplary embodiment of FIG. 3, the user device data storage 320 is located internal to the user device memory 310 of the user device 106. Additionally, or alternatively, the user device data storage 320 are located external to the user device 106 such as, for example, an external hard drive connected to the user device user interface 304 (not shown). In a further embodiment, the user device data storage 320 is located external and connected to the user device 106 through a network and accessed via the user device network interface 306 (not shown).

In operation, information for storage, such as the patient data and the approval to adjust the medical input parameters, in the user device data storage 320 is entered via the user device user interface 304. Alternatively, information, for example, the patient data for storage in the user device data storage 320 is received from the server 102 via the user device transceiver 302. In some embodiments, the data stored in the user device data storage 320, for example, the patient data and the approval to adjust the medical input parameters, is further provided to the database 110 and/or the server 102 for optimizing the medical procedure.

The user device processor 308 is a hardware device for executing software instructions now known or in the future developed. In an embodiment, the user device processor 308 is any custom-made or commercially available processor, a central processing unit (CPU), an auxiliary processor among several processors associated with the user device processor 308, a semiconductor-based microprocessor, or generally any device for executing software instructions. When the user device 106 is in operation, the user device processor 308 is configured to execute software stored within the user device memory 310, to communicate data to and from the user device memory 310, and to generally control operations of the user device 106 pursuant to the software instructions. The detailed functionalities and operations of the user device processor 308 will be described hereinafter in greater detail.

The description below discusses the functions and operations performed by the respective server 102, imaging device 104, user device 106, and IoT capable medical devices 108. Although the description below discusses the functions and operations performed by the respective server 102, imaging device 104, user device 106, and IoT capable medical devices 108, a person skilled in the art would appreciate that, in some embodiments, the functions and operations of the server 102, the imaging device 104, the user device 106, and the IoT capable medical devices 108 are performed in a single device or in a distributed manner by two or more devices without limiting the scope of the claimed subject matter.

Figure 4:
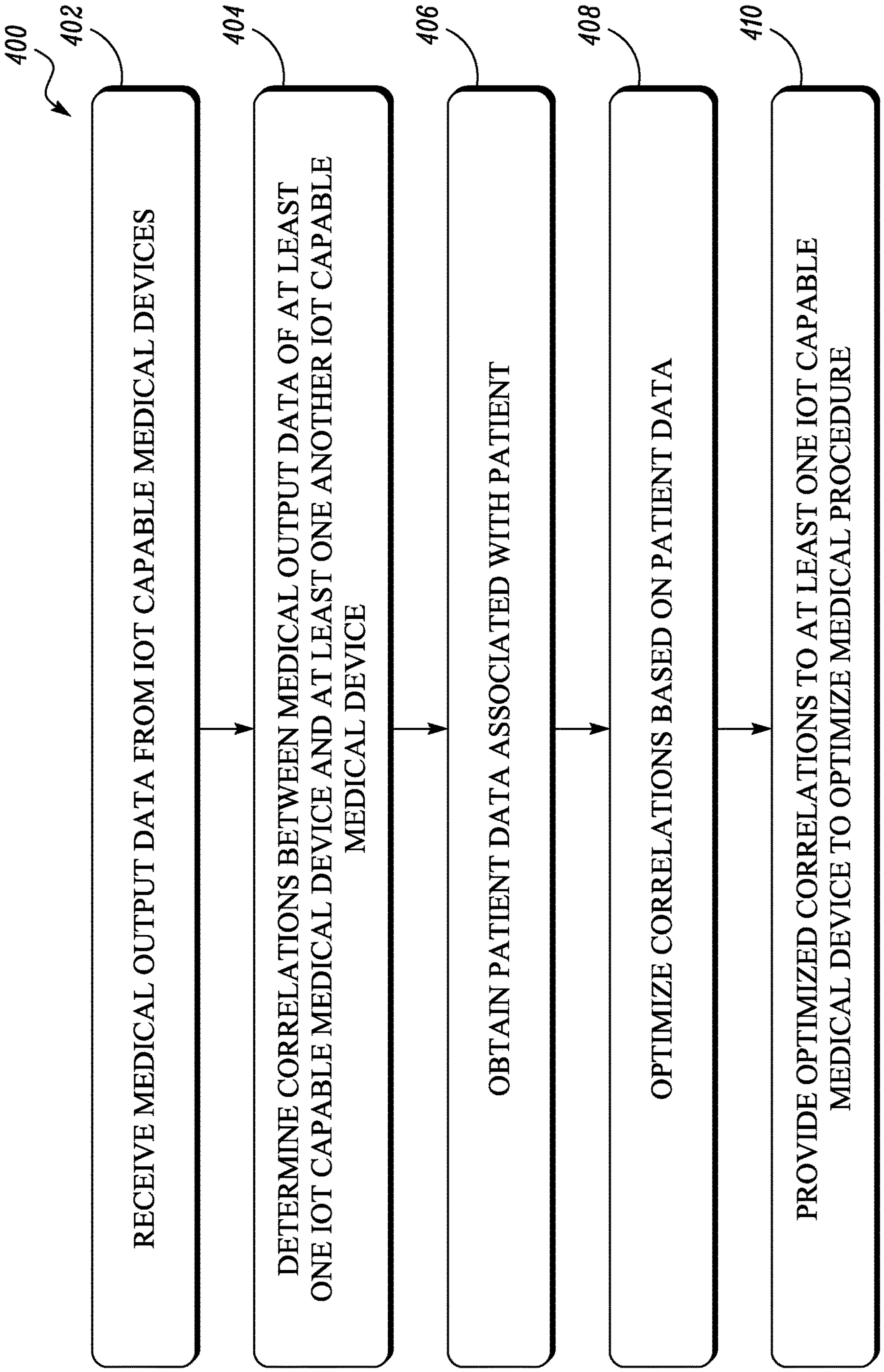
FIG. 4 depicts a flow diagram for optimizing the medical procedure using the IoT capable medical devices, in accordance with some embodiments.

FIG. 4 depicts a flow diagram of a method 400 for continuously optimizing the medical procedure. The method 400 begins at 402, with the server 102 receiving the medical output data associated with the medical procedure from the IoT capable medical devices 108 via the server transceiver 202. To this end, each IoT capable medical device 108 provides its medical output data associated with the medical procedure to the server 102. For example, the anesthesia machine 108-1 provides the medical output data, such as, a delivery rate, a proportion, a concentration, and the like of medical gases provided to the patient to the server 102. Similarly, the electrophysiological monitoring device 108-2 provides the medical output data, such as, electrical activity associated with the brain, the nerve pathways, the muscle and the like of the patient to the server 102. Similarly, the smart bed 108-4 provides the medical output data, such as, data associated with an angle and/or rotation of the smart bed 108-4 to the server 102.

In some embodiments, the medical output data includes medical output data associated with one or more medical procedures performed prior to the medical procedure and provided by the IoT capable medical devices 108. The one or more medical procedures correspond to the medical procedure. For example, when the medical procedure is a spinal surgery, the one or more medical procedures performed prior to the medical procedure also correspond to one or more spinal surgeries. The server 102, for example, the server processor 210, obtains the medical output data associated with the one or more medical procedures performed prior to the medical procedure from the server data storage 220 and/or the database 110.

At 404, the server processor 210 of the server 102 determines one or more correlations between the medical output data of at least one IoT capable medical device 108 of the plurality of IoT capable medical devices 108 and at least one another IoT capable medical device 108 of the plurality of IoT capable medical devices 108 using the one or more machine learning models. In accordance with various embodiments, the correlations correspond to a relationship of one or more of the medical output data, the medical input parameters, and an operation of the at least one IoT capable medical device 108 with one or more of the medical output data, the medical input parameters, and an operation of the at least one another IoT capable medical device 108. In an exemplary embodiment, the correlations correspond to a relationship between the medical output data of the at least one IoT capable medical device 108 and the at least one another IoT capable medical device 108. For example, the correlations represent whether and how much the medical output data of the at least one IoT capable medical device 108 changes with a change in the medical output data of the at least one another IoT capable medical device 108. To this end, the server processor 210 analyzes the medical output data of the at least one IoT capable medical device 108 with the medical output data of the at least one another IoT capable medical device 108 and determines the correlations between the medical output data. As discussed above, the medical output data may correspond to the medical procedure and/or the one or more medical procedures performed prior to the medical procedure.

In an exemplary embodiment, the server 102 determines one or more correlations between the medical output data, such as the delivery rate, the proportion, the concentration, and the like of medical gases provided by the anesthesia machine 108-1 with the medical output data, such as the electrical activity associated with the brain, the nerve pathways, the muscle and the like provided by the electrophysiological monitoring device 108-2. Additionally, or alternatively, the server 102 determines one or more correlations between the medical output data, such as, the data associated with the angle and/or the rotation of the smart bed 108-4 provided by the smart bed 108-4 with the medical output data, such as, the electrical activity associated with the brain, the nerve pathways, the muscle and the like provided by the electrophysiological monitoring device 108-2. For example, a correlation may indicate that a reduction in the angle of the smart bed 108-4 during the scoliosis reduction reduces the electrical activity associated with the brain, the nerve pathways, and the muscle provided by the electrophysiological monitoring device 108-2. Similarly, another correlation may indicate that an increase in one of the delivery rate, the proportion, and the concentration, of medical gases provided by the anesthesia machine 108-1 reduces the electrical activity associated with the brain, the nerve pathways, and the muscle provided by the electrophysiological monitoring device 108-2.

In accordance with various embodiments, a value of a correlation coefficient for each of the one or more correlations is greater than a predetermined threshold value. To this end, the machine learning module 222 of the server processor 210 determines a correlation coefficient for each of the one or more correlations between the medical output data of the at least one IoT capable medical device 108 and the at least one another IoT capable medical device 108. The correlation coefficient corresponds to a value that indicates a value the medical output data of the at least one IoT capable medical device 108 changes with the change in the medical output data of the at least one another IoT capable medical device 108. It would be appreciated that the determination of a correlation coefficient of a correlation is well-known in the art and is not described here for the sake of brevity.

The machine learning module 222 of the server processor 210 then identifies the correlation coefficients having values greater than the predetermined threshold. The predetermined threshold is any number defined by the user based on the preference of the user. In some embodiments, the predetermined threshold is a number determined by the server processor 210 based on the medical output data from the IoT capable medical devices 108 associated with the one or more medical procedures performed prior to the medical procedure. The machine learning module 222 of the server processor 210 further identifies correlation(s) having values of the correlation coefficients greater than the predetermined threshold as the one or more correlations (and discards other correlations with the correlation coefficients having values less than or equal to the predetermined threshold.) In accordance with various embodiments, the one or more correlations are correlations that are relevant for optimizing the medical procedure. In such cases, the discarded other correlations are considered noise or weak correlations that are not relevant for optimizing the medical procedure.

At 406, the server processor 210 obtains the patient data associated with the patient undergoing the medical procedure. In an embodiment, when the patient data is stored in the server data storage 220, the server processor 210 obtains the patient data from the server data storage 220. In another embodiment, when the patient data is stored in the user device data storage 320 or the database 110, the server processor 210 obtains the patient data from the user device data storage 320 or the database 110 via the server transceiver 202.

At 408, the server 102 optimizes the one or more correlations between the medical output data of the at least one IoT capable medical device and the at least one another IoT capable medical device to obtain one or more optimized correlations based on the patient data using the one or more machine learning models. To this end, the machine learning module 222 of the server processor 210 analyzes the patient data and utilizes the analyzed patient data to optimize the one or more correlations. In an exemplary embodiment, when the correlation indicates that an increase in the delivery rate, the proportion, and the concentration of medical gases provided by the anesthesia machine 108-1 reduces the electrical activity associated with the brain, the nerve pathways, and the muscle provided by the electrophysiological monitoring device 108-2, the machine learning module 222 of the server processor 210 optimizes this correlation based on the patient data, such as the metabolism rate of the patient. For example, for a patient with high metabolism rate, the machine learning module 222 of the server processor 210 may optimize the correlation to increase the concentration of oxygen to regulate the electrical activity associated with the brain, the nerve pathways, and the muscle in the patients with high metabolism rate. Similarly, when the correlation indicates that a reduction in the angle of the smart bed 108-4 during the scoliosis reduction reduces the electrical activity associated with the brain, the nerve pathways, and the muscle provided by the electrophysiological monitoring device 108-2, the machine learning module 222 of the server processor 210 optimizes this correlation based on the patient data, such as the height of the patient.

In some embodiments, the server 102 associates the one or more correlations and/or the one or more optimized correlations with one or more of a medical practitioner identifier identifying a medical practitioner performing the medical procedure and a medical room identifier identifying a medical procedure room for performing the medical procedure. To this end, the server processor 210 receives one or more inputs such as, the medical practitioner identifier that corresponds to the medical practitioner performing the medical procedure and the medical procedure room identifier that corresponds to the medical room in which the medical procedure is performed, from the medical practitioner and associates the one or more correlations and/or the one or more optimized correlations with the medical practitioner identifier and/or the medical room identifier.

In some embodiments, the server processor 210 of the server 102 processes the plurality of video/image frames to identify the medical practitioner and/or the medical procedure room in the plurality of video/image frames. In accordance with various embodiments, the server processor 210 of the server 102 utilizes the image processing software to identify the medical practitioner and the medical procedure room. For example, the image processing software when executed by the server processor 210 identifies the medical practitioner and the medical procedure room by comparing the captured images of the medical practitioner and the medical procedure room with images stored in one or more online image libraries. The server processor 210 of the server 102 then displays the medical practitioner identifier identifying the medical practitioner and the medical procedure room identifier identifying the medical procedure room on the server display 208 or the user device display 312 for verification by the user. In some embodiments, the server processor 210 upon receiving an indication from the user that the displayed identification is not verified, enables the user to provide the medical practitioner identifier identifying the medical practitioner and a medical procedure room identifier identifying the medical procedure room via the server user interface 204 or the user device user interface 304. In some embodiments, for example, when a medical practitioner or the medical procedure room is not identified or verified, the server processor 210 of the server 102 prompts the user (for example, the medical practitioner) to enter the medical practitioner identifier and/or the medical procedure room identifier of the respective unidentified medical practitioner and/or the medical procedure room via the server user interface 204 or the user device user interface 304. In some embodiments, the machine learning module 222 of the server 102 continuously updates the medical practitioner identifier and/or the medical procedure room identifier based on inputs, such as, the indication, the medical practitioner identifier, and the medical procedure room identifier received from the user.

At 410, the server 102 provides, via the server transceiver 202, the one or more optimized correlations to the at least one IoT capable medical device 108 to optimize the medical procedure by adjusting medical input parameters associated with the at least one IoT capable medical device 108 based on the one or more optimized correlations with the at least one another IoT capable medical device 108. For example, the server 102 provides the optimized correlation to the smart bed 108-4 to optimize the medical procedure by adjusting its medical input parameters, such as, the angle based on the one or more optimized correlations with the electrical activity associated with the brain, the nerve pathways, and the muscle provided by the electrophysiological monitoring device 108-2.

Upon receiving the optimized correlations, the at least one IoT capable medical device 108 obtains the medical output data associated with the medical procedure from the at least one another IoT capable medical device 108 and adjusts its medical input parameters based on the obtained medical output data of the at least one another IoT capable medical device 108 and the one or more optimized correlations. In accordance with various embodiments, the at least one IoT capable medical device 108 adjusts its medical input parameters based on the obtained medical output data of the at least one another IoT capable medical device 108 and the one or more optimized correlations such that the medical output data of the at least one another IoT capable medical device 108 remains regulated or within a predefined range. The predefined range is a range defined by the user (for example, the medical practitioner) or determined by the server processor 210 based on the medical output data from the IoT capable medical devices 108 associated with the one or more medical procedures performed prior to the medical procedure. The predefined range corresponds to a range that is considered safe for a patient during the medical procedure. For example, upon receiving the optimized correlations, the smart bed 108-4 obtains the electrical activity associated with the brain, the nerve pathways, and the muscle from the electrophysiological monitoring device 108-2 and adjusts its medical input parameters, such as, the angle based on the one or more optimized correlations and the electrical activity provided by the electrophysiological monitoring device 108-2 such that the electrical activity remains regulated or within the predefined range.

In some embodiments, the at least one IoT capable medical device 108 adjusts its one or more medical input parameters by providing a notification to the user, via the user device 106 or the server 102 to approve adjustment of the one or more medical input parameters. To this end, the at least one IoT capable medical device 108, for example, via the server 102, displays the notification on the user device display 312 of the user device 106 or the server display 208 of the server 102 for receiving approval from the user. Upon receiving the approval, the at least one IoT capable medical device 108 adjusts its medical input parameters. In some embodiments, when the user does not approve the adjustment of the medical input parameters, a rejection notification is transmitted to the machine learning module 222 of the server 102 that is further utilized by the machine learning module 222 to optimize the correlations.

Figure 5:
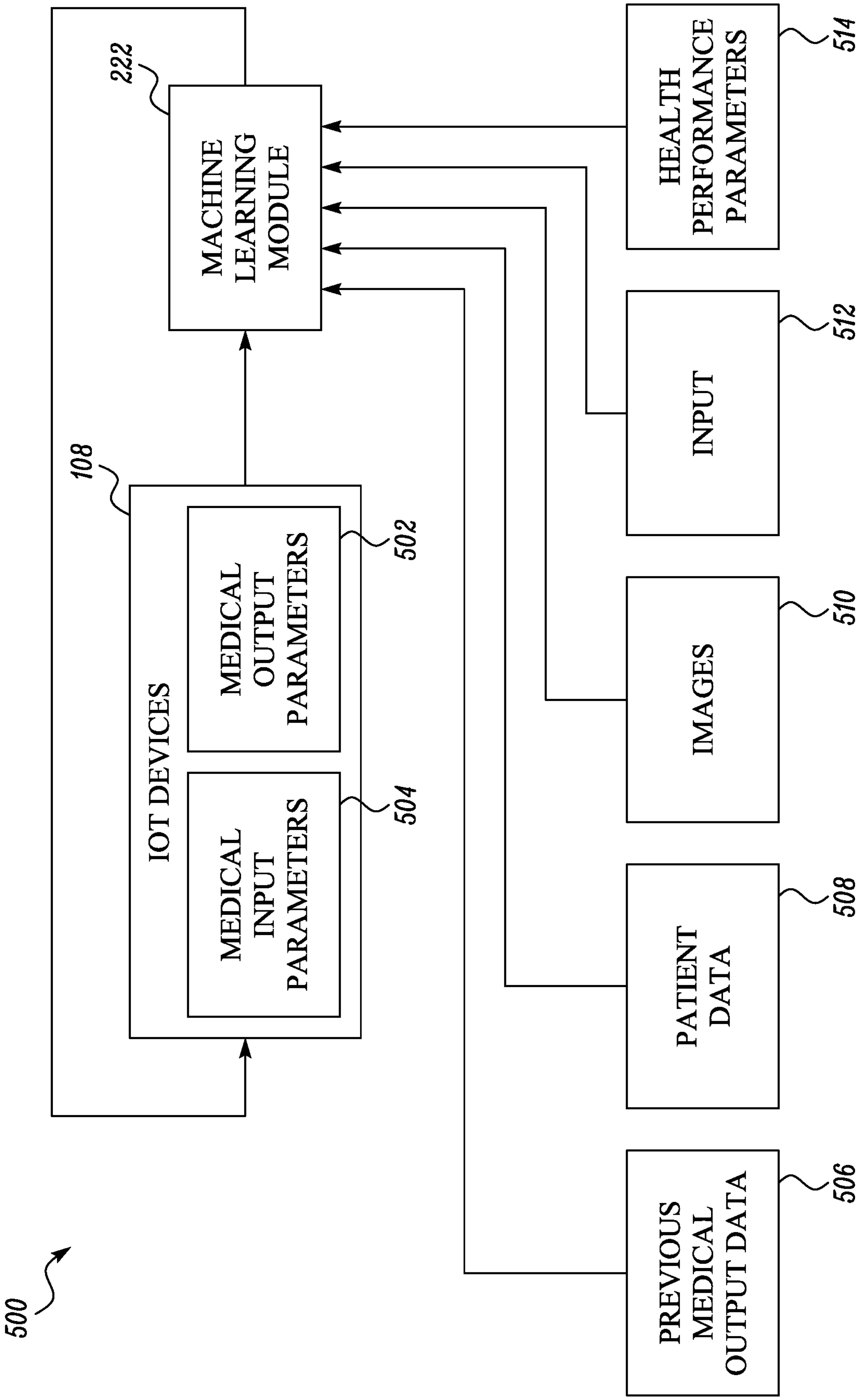
FIG. 5 is a block diagram of an optimization cycle for optimizing the medical procedure, in accordance with some embodiments.

In accordance with various embodiments, the machine learning module 222 of the server 102 is configured to continuously optimize the medical procedure using the one or more machine learning models. The continuous optimization of the medical procedure is described herein with reference to FIG. 5. Referring to FIG. 5, the optimization cycle 500 associated with the optimization of the medical procedure is described. As shown in FIG. 5, the server 102 (for example, the machine learning module 222 of the server processor 210) obtains the medical output data 502 associated with the IoT capable medical devices 108 and determines the correlations based on the medical output data 502.

In some embodiments, the server 102 (for example, the machine learning module 222 of the server processor 210) also obtains the medical output data 506 from the IoT capable medical devices 108 associated with the one or more medical procedures performed prior to the medical procedure and optimizes the one or more correlations, as described in detail in the foregoing description. In some cases, the one or more medical procedures performed prior to the medical procedure correspond to the medical procedures performed by the same or different medical practitioner(s) in the same or different medical procedure room. In such cases, the correlations determined by the machine learning module 222 are not specific to any medical practitioner or medical procedure room. In some other embodiments, the one or more medical procedures performed prior to the medical procedure correspond to the medical procedures performed by the same medical practitioner(s) in the same or different medical procedure room. In such cases, the correlations determined by the machine learning module 222 are specific to the medical practitioner performing the medical procedure. Additionally, or alternatively, the one or more medical procedures performed prior to the medical procedure correspond to the medical procedures performed by the same or different medical practitioner(s) in the same medical procedure room. In such cases, the correlations determined by the machine learning module 222 are specific to the medical procedure room in which the medical procedure is performed. Additionally, or alternatively, the one or more medical procedures performed prior to the medical procedure corresponds to the medical procedures performed by the same medical practitioner(s) in the same medical procedure room. In such cases, the correlations determined by the machine learning module 222 are specific to the medical practitioner performing the medical procedure and the medical procedure room in which the medical procedure is performed.

The server 102 (for example, the machine learning module 222 of the server processor 210) further obtains the patient data 508 and optimizes the one or more correlations based on the obtained data, as described in detail in the foregoing description. In some embodiments, the server 102 then provides the optimized correlations to the IoT capable medical devices 108 to adjust the medical input parameters 504 of the IoT capable medical devices 108.

In some embodiments, the server 102 (for example, the machine learning module 222) receives one or more inputs, such as, but not limited to, at least an image captured by the imaging device 104, the voice command provided during the medical procedure, or the user input received via the user device 106 associated with the medical procedure. The server 102 (for example, the machine learning module 222) then analyzes the one or more inputs to optimize the one or more correlations and/or the optimized one or more correlations based on the one or more inputs using the one or more machine learning models.

In some embodiments, the server 102 (for example, the machine learning module 222) obtains one or more images 510 captured by the imaging device 104 and optimizes the one or more correlations and/or the optimized one or more correlations based on the one or more images 510. To this end, the server processor 210 of the server 102 identifies the medical item(s) and/or the medical practitioner(s) during the medical procedure and determines the parameters associated with the identified medical item(s) and/or the medical practitioner(s) during the medical procedure using the image processing software. The machine learning module 222 then optimizes the correlations based on the determined parameters. For example, the server processor 210 determines the positioning of the medical practitioner during the scoliosis reduction and optimizes the correlations based on the positioning of the medical practitioner. In some embodiments, the server 102 then provides the optimized correlations to the IoT capable medical devices 108 to adjust the medical input parameters 504 of the IoT capable medical devices 108.

In some embodiments, the server 102 (for example, the machine learning module 222) obtains inputs 512, such as, voice commands from the user (for example, the medical practitioner) during the medical procedure and optimizes the one or more correlations and/or the optimized one or more correlations based on the user inputs. For example, when the voice command indicates that the angle of the smart bed 108-4 should not be less than a defined value, the machine learning module 222 optimizes the correlations such that the angle of the smart bed 108-4 always remains greater than or equal to the defined value. In some embodiments, the server 102 then provides the optimized correlations to the IoT capable medical devices 108 to adjust the medical input parameters 504 of the IoT capable medical devices 108.

In some embodiments, the server 102 (for example, the machine learning module 222) obtains one or more health performance parameters 514 associated with a performance of the medical procedure. The server 102 (for example, the machine learning module 222) determines a deviation of each of the one or more health performance parameters from a corresponding desired health performance parameter defined by the user and optimizes the one or more correlations or the one or more optimized correlations based on the determined deviation using the one or more machine learning models. In some embodiments, the server 102 then provides the optimized correlations to the IoT capable medical devices 108 to adjust the medical input parameters 504 of the IoT capable medical devices 108.

The system and the method of the present disclosure are directed towards continuously optimizing the medical procedure to improve the accuracy and efficiency of the medical procedure. By determining the one or more correlations between the medical output data of the IoT capable medical devices 108 and further optimizing the correlations based on the patient data, patient-specific optimization of the medical procedure can be achieved in real-time. The adjustments of the medical input parameters of the IoT capable medical devices based on the determined correlations also reduce any chances of human error during the medical procedure. Moreover, consideration of various parameters, such as, the one or more medical procedures performed prior to the medical procedure, the user input, and the health performance parameters further optimizes the correlations thereby leading to improved efficiency of the medical procedure.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises", "comprising", "has", "having", "includes", "including," "contains", "containing", or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element preceded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (for example, comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A system for continuously optimizing a live medical procedure, the system comprising:

a plurality of internet-of-things (IoT) capable medical devices, each IoT capable medical device of the plurality of IoT capable medical devices configured to provide medical output data associated with the live medical procedure, wherein the plurality of IoT capable medical devices includes a first IoT capable medical device corresponding to a smart bed and a second IoT capable medical device corresponding to an electrophysiological monitoring device; and a server communicatively coupled to the plurality of IoT capable medical devices, the server is configured to:

receive, by a server transceiver, the medical output data associated with the live medical procedure from the plurality of IoT capable medical devices;

determine, by a server processor, one or more correlations between the medical output data of the first IoT capable medical device of the plurality of IoT capable medical devices and the second IoT capable medical device of the plurality of IoT capable medical devices using one or more machine learning models;

obtain, by the server processor, patient data associated with a patient undergoing the live medical procedure;

optimize, by the server processor, the one or more correlations between the medical output data of the first IoT capable medical device and the second IoT capable medical device to obtain one or more optimized correlations based on the patient data using the one or more machine learning models;

provide, by the server transceiver, the one or more optimized correlations to the first IoT capable medical device; and repeat the receiving, the determining, the obtaining, the optimizing, and the providing steps during the live medical procedure, wherein, upon receiving the one or more optimized correlations, the first IoT capable medical device is configured to:

determine a predefined range corresponding to the medical output data of the second IoT capable medical device;

obtain the medical output data of the second IoT capable medical device, wherein the medical output data of the second IoT capable medical device corresponds to an electrical activity associated with the brain, the nerve pathways, and the muscle of the patient;

and adjust an angle of the first IoT capable medical device based on the determined predefined range, the obtained medical output data of the second IoT capable medical device, and the one or more received optimized correlations such that the electrical activity is maintained within the determined predefined range.

2. The system as claimed in claim 1, wherein a value of a correlation coefficient for each of the one or more correlations is greater than a predetermined threshold value.

3. The system as claimed in claim 1, wherein the server is further configured to:

receive, by the server transceiver, one or more inputs associated with the live medical procedure, wherein the one or more inputs includes at least an image captured by an image capturing device, a voice command provided during the live medical procedure, or a user input received via a user device; and analyze, by the server processor, the one or more inputs to optimize the one or more correlations or the optimized one or more correlations based on the one or more inputs using the one or more machine learning models.

4. The system as claimed in claim 1, wherein the patient data includes a height of the patient.

5. The system as claimed in claim 1, wherein the one or more correlations includes correlations between the medical output data, from a plurality of IoT capable medical devices, associated with one or more medical procedures performed prior to the live medical procedure.

6. The system as claimed in claim 1, wherein the first IoT capable medical device is configured to adjust the angle by:

providing a notification on a user device associated with a medical practitioner to approve adjustment of the angle; and adjusting the angle upon receiving the approval.

7. The system as claimed in claim 1, wherein the server is further configured to:

associate, by the server processor, the one or more correlations or the one or more optimized correlations with one or more of a medical practitioner identifier identifying a medical practitioner performing the live medical procedure and a medical room identifier identifying a medical procedure room for performing the live medical procedure.

8. The system as claimed in claim 1, wherein the server is further configured to:

acquire, by the server processor, one or more health performance parameters associated with a performance of the live medical procedure;

determine, by the server processor, that the live medical procedure is being performed suboptimally when the one or more health performance parameters deviate from a corresponding desired health performance parameter;

automatically update, by the server processor, the one or more optimized correlations based on the deviation such that the one or more health performance parameters correspond to the desired health performance parameter; and provide, by the server transceiver, the one or more optimized correlations updated based on the deviation to the first IoT capable medical device.

9. A method for continuously optimizing a live medical procedure, the method comprising:

receiving, by a server, medical output data associated with the live medical procedure from a plurality of internet-of-things (IoT) capable medical devices, wherein the plurality of IoT capable medical devices includes a first IoT capable medical device corresponding to a smart bed and a second IoT capable medical device corresponding to an electrophysiological monitoring device;

determining, by the server, one or more correlations between the medical output data of the first IoT capable medical device of the plurality of IoT capable medical devices and the second IoT capable medical device of the plurality of IoT capable medical devices using one or more machine learning models;

obtaining, by the server, patient data associated with a patient undergoing the live medical procedure;

optimizing, by the server, the one or more correlations between the medical output data of the first IoT capable medical device and the second IoT capable medical device to obtain one or more optimized correlations based on the patient data using the one or more machine learning models;

providing, by the server, the one or more optimized correlations to the first IoT capable medical device;

repeating the steps performed by the server during the live medical procedure;

obtaining, by the first IoT capable medical device, the medical output data of the second IoT capable medical device, wherein the medical output data of the second IoT capable medical device corresponds to an electrical activity associated with the brain, the nerve pathways, and the muscle of the patient;

determining, by the first IoT capable medical device, a predefined range corresponding to the medical output data of the second IoT capable medical device; and adjusting, by the first IoT capable medical device, an angle of the first IoT capable medical device based on the determined predefined range, the obtained medical output data of the second IoT capable medical device, and the one or more received optimized correlations such that the electrical activity is maintained within the predefined range.

10. The method as claimed in claim 9, wherein a value of a correlation coefficient for each of the one or more correlations is greater than a predetermined threshold value.

11. The method as claimed in claim 9, further comprising:

receiving, by the server, one or more inputs associated with the live medical procedure, wherein the one or more inputs includes at least an image captured by an image capturing device, a voice command provided during the live medical procedure, or a user input received via a user device; and analyzing, by the server, the one or more inputs to optimize the one or more correlations or the optimized one or more correlations based on the one or more inputs using the one or more machine learning models.

12. The method as claimed in claim 9, wherein the patient data includes a height of the patient.

13. The method as claimed in claim 9, wherein the one or more correlations includes correlations between the medical output data, from a plurality of IoT capable medical devices, associated with one or more medical procedures performed prior to the live medical procedure.

14. The method as claimed in claim 9, wherein adjusting the angle further includes:

providing a notification on a user device associated with a medical practitioner to approve adjustment of the angle of the smart bed; and adjusting the angle of the smart bed upon receiving the approval.

15. The method as claimed in claim 9, further comprising:

associating, by the server, the one or more correlations or the one or more optimized correlations with one or more of a medical practitioner identifier identifying a medical practitioner performing the live medical procedure and a medical room identifier identifying a medical procedure room for performing the live medical procedure.

16. The method as claimed in claim 9, further including:

acquiring, by the server, one or more health performance parameters associated with a performance of the live medical procedure;

determining, by the server, that the live medical procedure is being performed suboptimally when the one or more health performance parameters deviate from a corresponding desired health performance parameter;

automatically updating, by the server, the one or more optimized correlations based on the deviation such that the one or more health performance parameters correspond to the desired health performance parameter; and providing, by the server, the one or more optimized correlations updated based on the deviation to the first IoT capable medical device.

* * * * *